United States Patent
Nakamura et al.

(10) Patent No.: US 6,563,633 B2
(45) Date of Patent: May 13, 2003

(54) MICROSCOPE FOR MRI AND SUPPORT STAND FOR MRI

(75) Inventors: Katsushige Nakamura, Hachioji (JP); Masao Doi, Fuchu (JP); Masakazu Nakamura, Mitaka (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 0 days.

(21) Appl. No.: 09/845,269

(22) Filed: May 1, 2001

(65) Prior Publication Data

US 2001/0038489 A1 Nov. 8, 2001

(30) Foreign Application Priority Data

May 2, 2000 (JP) .......................... 2000-171277
Feb. 2, 2001 (JP) .......................... 2001-027154

(51) Int. Cl.$^7$ .............................................. G02B 21/00
(52) U.S. Cl. ...................... 359/368; 359/384; 248/585
(58) Field of Search ................... 359/368, 382, 359/384; 248/123.11, 280.11, 281.11, 585

(56) References Cited

U.S. PATENT DOCUMENTS

| 3,967,723 A | * | 7/1976 | Beckham ................. 198/403 |
| 5,140,458 A | * | 8/1992 | Takagi et al. ............. 359/380 |
| 5,528,417 A | | 6/1996 | Nakamura ................ 359/384 |
| 5,805,335 A | * | 9/1998 | Fukaya et al. ............ 359/384 |
| 6,322,554 B1 | * | 11/2001 | Tomita ....................... 606/10 |

* cited by examiner

*Primary Examiner*—Mark A. Robinson
(74) *Attorney, Agent, or Firm*—Oblon, Spivak, McClelland, Maier & Neustadt, P.C.

(57) ABSTRACT

A microscope suitable for use together with MRI, and a support stand for the microscope are provided. A microscope 1 is a non-magnet type where any electric motor is not used, and hence does not induce fluctuations of magnetic field having effects on image quality of an MRI 3 by focusing or zooming. Hence, the microscope of the invention is suitable for use together with MRI 13. Since a clutch C is of non-magnet type, a support stand 2 does not induce changes in the surrounding magnetic field environments if the clutch is operated, and hence it is suitable for use, for example, in proximity to the MRI.

12 Claims, 9 Drawing Sheets

MICROSCOPE FOR MRI AND SUPPORT STAND FOR MRI

BACKGROUND OF THE INVENTION

The present invention relates to a microscope suitable for use in proximity to an MRI apparatus, and a support stand for supporting the microscope.

In the field of neurosurgery or cardiosurgery, microscopic operation where an operation is conducted while observing the ailing site by a microscope is known. Such a microscopic operation is generally performed on the basis of tomographic imaging information of CT, MRI, etc., and in particular the MRI (image processing apparatus utilizing magnetic resonance imaging principle) is widely employed because it is safer than the X-ray CT.

SUMMARY OF THE INVENTION

However, in the same operating room, if the so-called open MRI and a microscope are used together, the magnetic field is changed when focusing or zooming the microscope, and noises are mixed in an MRI monitor, and accurate information of the site may not be obtained. Also, if driving means is used in a support stand for supporting the microscope, the magnetic field is changed by its electric motor, or if an electromagnetic clutch is used as clutch means, the magnetic field is similarly changed by the electromagnetic clutch, and noises are mixed in an image.

The present invention has been made in view of such problems of the prior art, and an object thereof is to provide a microscope suitable for use with an MRI, and a support stand for the microscope.

A first aspect of the present invention relates to a microscope used in a room where an MRI is installed, and the microscope is characterized by being controlled by driving of an actuator which does not generate magnetic field.

According to a second aspect of the invention, focusing or zooming of the microscope is driven by an air motor, and can be also driven manually in case of emergency.

According to a third aspect of the invention, a turbine having a turbine shaft connected in the center is rotatably accommodated in a hollow space formed in a housing, and air is sent into the turbine from an feed port formed in the housing, and exhausted from the exhaust port, and the air motor comprises the housing forming a hollow space, and the turbine rotatably accommodated in the hollow space, and therefore air is supplied into the turbine from the feed port and is exhausted, and when the air is supplied, the brake pad contacting with the turbine with a specific thrusting force is separated from the turbine by the pressure of the exhaust air so as to be in contact-free state.

A forth aspect of the invention relates to a support stand used in an MRI room where an MRI is installed, and the support stand comprises plural support arms, at least one rotary shaft for mounting the support arms, and a clutch for locking and releasing the rotary shaft, and the clutch is of non-magnet type.

DESCRIPTION OF THE PREFERRED EMBODIMENTS

Preferred embodiments of the invention are described below based on the accompanying drawings.

Figure 1:
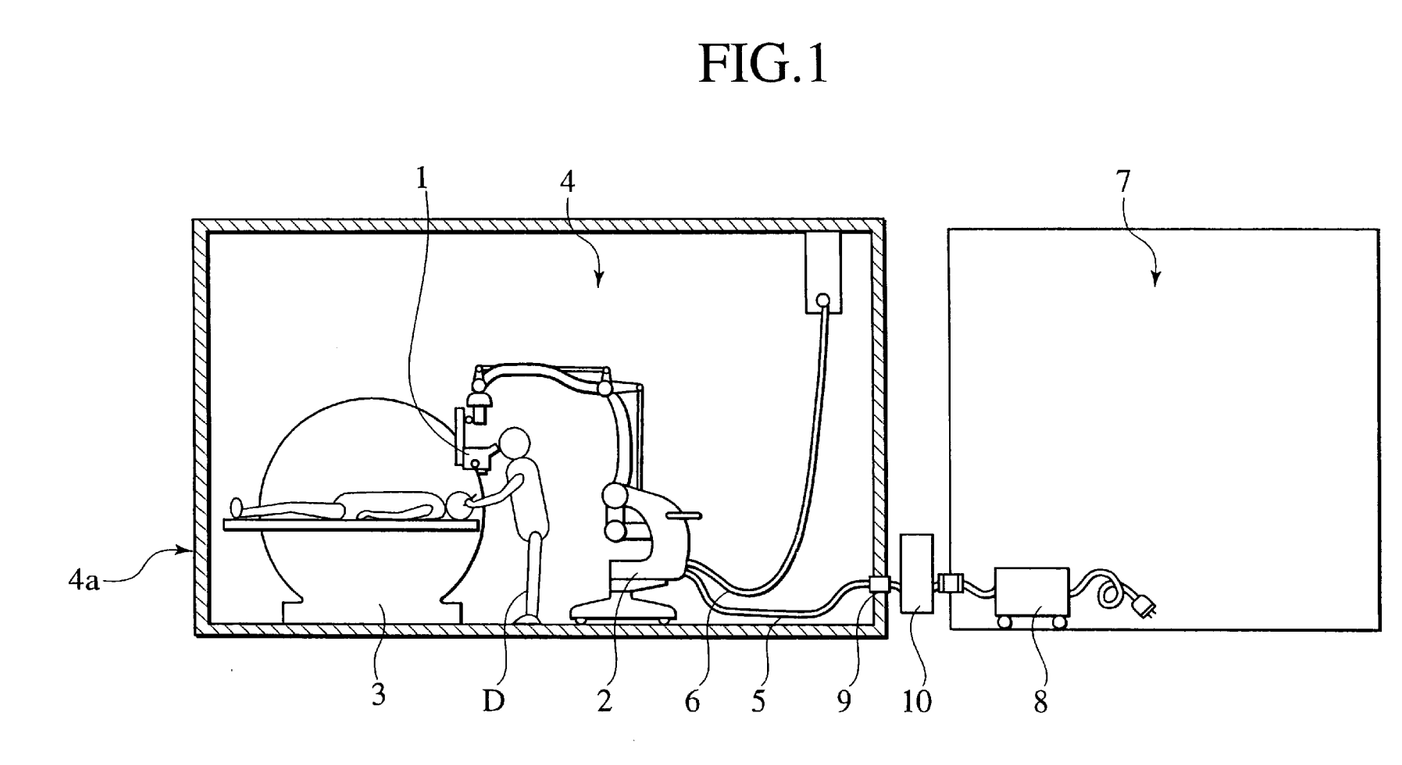
FIG. 1 is a schematic view showing the state of use of microscope for MRI and support stand in an embodiment of the invention.

FIG. 1 is a schematic view showing the state of use of microscope for MRI and support stand in an embodiment of the invention.

The microscope 1 for MRI and support stand 2 of the embodiment are used in microscopic operation using MRI (image processing apparatus utilizing magnetic resonance imaging principle) 3. The microscope 1 and support stand 2 does not contain magnet, and does not generate magnetic field, and the driving source is air or gas pressure.

Generally, in the MRI room, a high uniformity is required in the static magnetic field of the MRI apparatus in order to obtain a high image quality, and it is necessary to maintain a static magnetic field stationary in space by ultimately suppressing time variations of magnetic field environments around the apparatus. For this purpose, the movable microscope 1 and support stand 2 are formed of aluminum or other non-magnetic material in order to prevent fluctuations of magnetic field in the room. As the non-magnetic material, as far as a specified strength is assured, brass, copper, stainless steel, ceramic or resin may be partly used.

The microscope 1 is driven by an air motor which does not generate magnetic field, instead of an electric motor which generates magnetic field noise, and the support stand 2 is similarly driven by an air clutch. Accordingly, by using the microscope 1 and support stand 2 of the embodiment in the microscopic operation, the peripheral magnetic field environments are not changed, and noise-free images of MRI are always obtained.

In an actual operation, in order to achieve complete electromagnetic shield in operating room 4 with the MRI 3, shielding panels are used in all walls 4a of the operating room 4. From the support stand 2, a cable 5 and a tube (also non-magnetic) 6 are extended and led outside of the operating room 4. The cable 5 connects between a small electromagnetic valve not shown in the support stand 2 (this small electromagnetic valve is very low in electromagnetic noise and hence has no effect) and a power source 8 installed in other room 7. This small electromagnetic valve controls to turn on and off the air to be supplied in the air motor of the microscope and the air clutch of the support stand 2. The cable 5 is connected by way of a shield connector 9 and a band pass filter 10, and completely shields electromagnetic noise at high frequency generated from the power source 8 in other room 7. The tube 6 for supplying air is connected to an air pump not shown, and the operating sound of the air pump is not transmitted directly to the operating room.

Microscope

Figure 2:
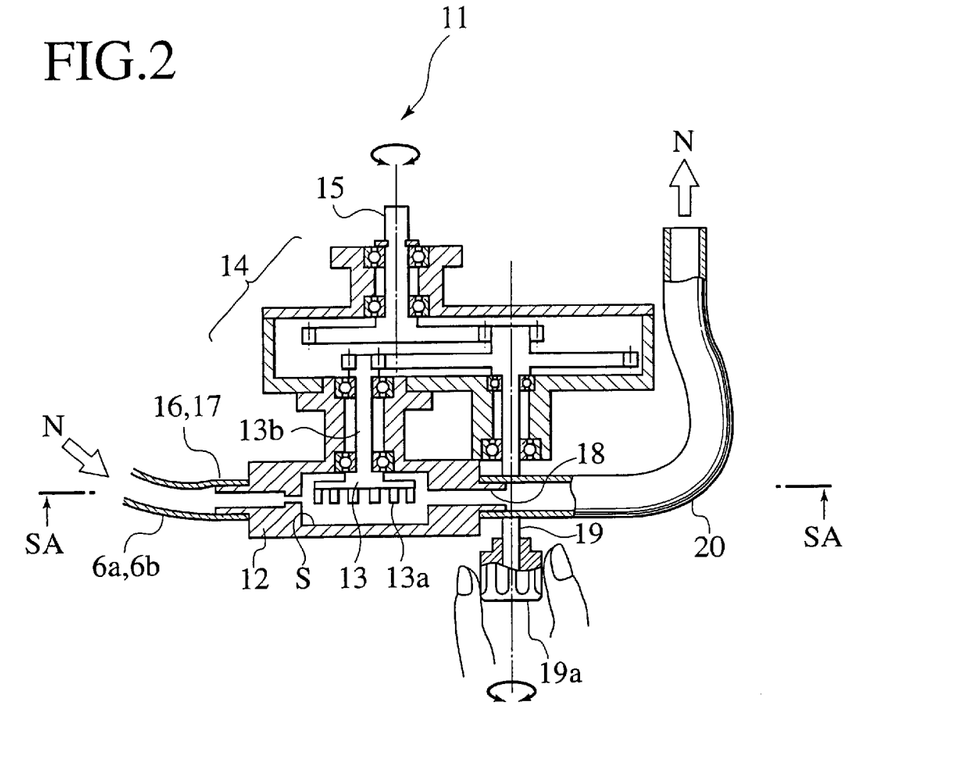
FIG. 2 is a sectional view showing an air motor of microscope for MRI.
Figure 3:
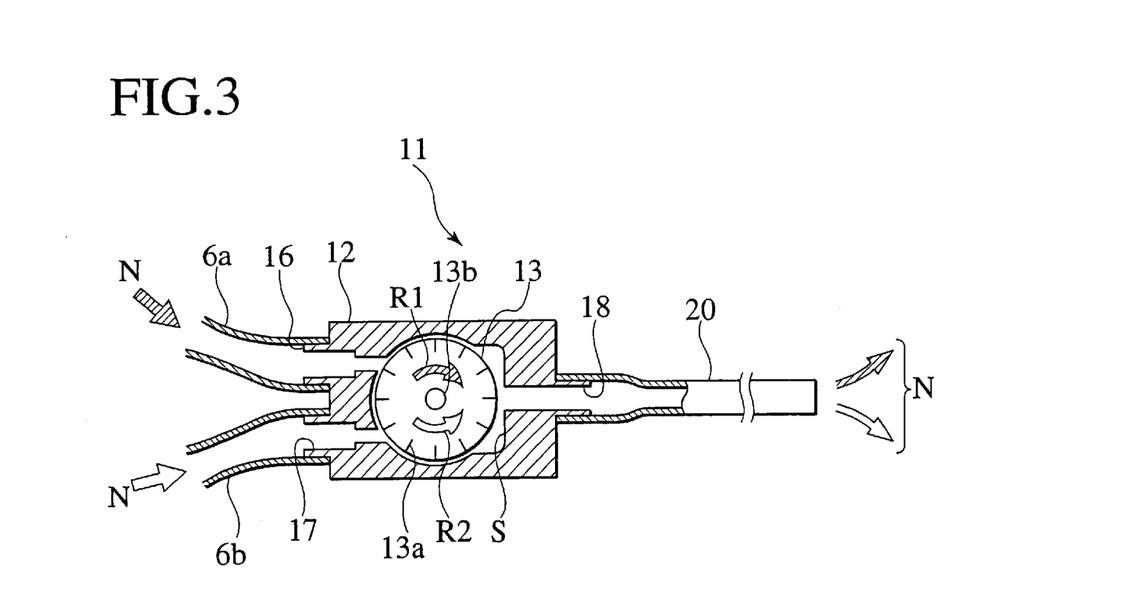
FIG. 3 is a sectional view along arrow SA—SA line in FIG. 2.

The microscope 1 of the embodiment is more specifically explained by referring to FIG. 2 to FIG. 5. FIG. 2 and FIG. 3 are schematic views showing an air motor 11 preferably used as a actuator of the microscope 1. The air motor 11 does not use any magnet, and hence does not generate magnetic field, and it is used as the driving unit of zooming means and focusing means indispensable in an optical system.

A hollow space S is formed in a housing 12, and a turbine 13 is accommodated in the space S. Plural blades 13a are radially formed on the side surface of the turbine 13, and a turbine shaft 13b is integrally formed in the center of the turbine 13. The housing 12 has two feed ports 16, 17, and one exhaust port 18 as shown in FIG. 3, which communicate with the space S. The two feed ports 16, 17 are arranged so that air may be supplied to mutually opposite sides of the blades.

Tubes 6a, 6b branched from the tube 6 through a small electromagnetic valve not shown are connected to the feed ports 16, 17, respectively, and an exhaust tube 20 is connected to the exhaust port 18. When rotating the turbine 13, either one of the feed ports 16, 17 is selected by the small electromagnetic valve not shown, and nitrogen gas is supplied as air N from the selected feed port 16 or 17, and torque is generated in direction R1 or R2 depending on the feed port, and the turbine 13 is put in rotation, and the supplied air N is exhausted from the exhaust port 18. That is, depending on the feed direction of the air N, the rotating direction R1 or R2 of the turbine 13 can be controlled.

When the turbine 13 is rotated by the air N and the turbine shaft 13b in the center of the turbine 13 is put in rotation, its rotating force is once decelerated in speed by a gear transmission 14, and is transmitted to an output shaft 15. The rotation of the output shaft 15 is further transmitted to the zooming means and focusing means.

The air motor 11 is provided with a manual input shaft 19 having knobs 19a at its end, so that the output shaft 15 can be rotated manually. Therefore, if any trouble should occur in the turbine 13 of the air motor 11 or supply route of air N to the turbine 13, the microscopic operation can be continued manually. Hence, the reliability as medical apparatus is high.

The exhaust tube 20 connected to the exhaust port 18 of the air motor 11 is guided into the adjacent support arm of the support stand 2. The exhaust tube 20 is extended to a remotest position from the microscope 1, so that the operating sound of the air pump transmitted indirectly from the air feed tube 6 may be reach up to the surgeon D. The exhaust tube 20 is a silicone tube of about 5 mm in diameter, and it is flexible and effectively absorbs air vibrations and plays a role of silencer.

Figure 4:
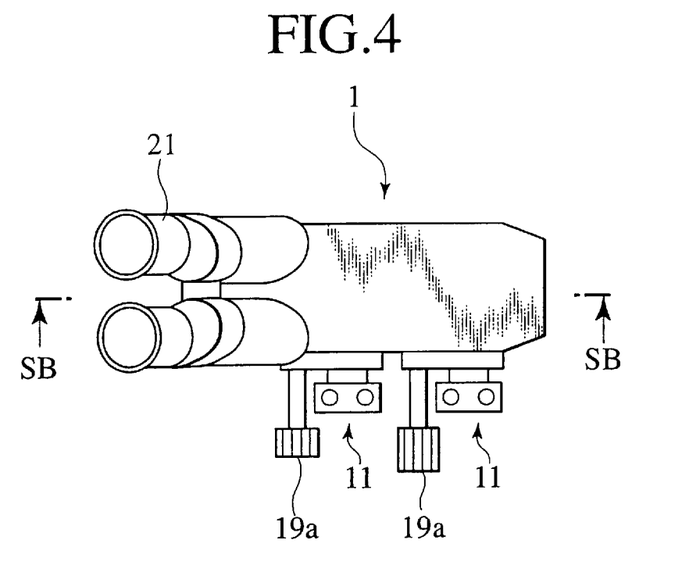
FIG. 4 is a plan view of microscope for MRI with an air motor.
Figure 5:
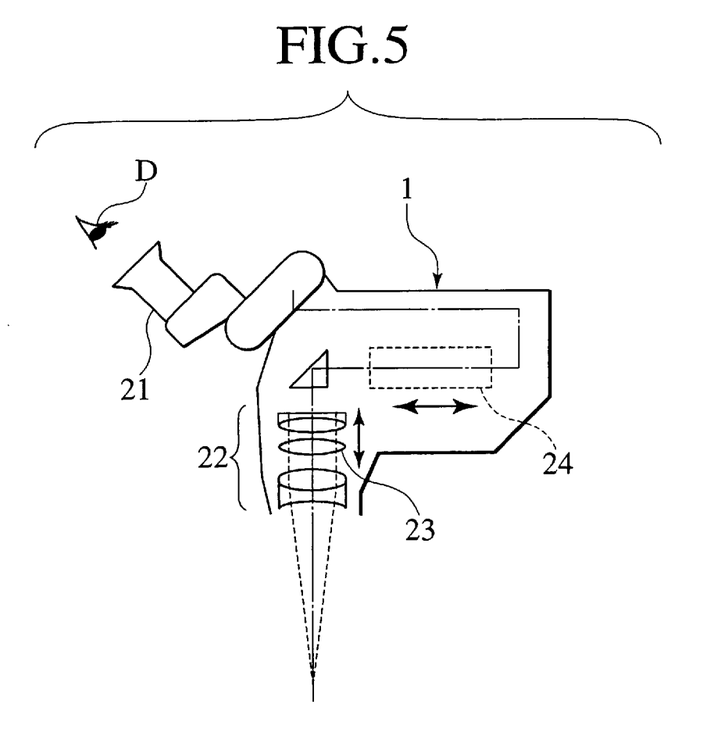
FIG. 5 is a sectional view along arrow SB—SB line in FIG. 4.

The microscope 1 having the air motor 11 is shown in FIG. 4 and FIG. 5. The surgeon D observes the ailing site through an ocular 21, and moves a focusing lens 23 and a zooming lens 24 of an objective 22 by the air motor 11, and adjusts the focus and magnification on the ailing site. If the air motor 11 does not operate normally due to troubles in the supply of air N or impellers 13a, the focus and magnification can be adjusted by using two knobs 19a provided at the side of the microscope 1. The knobs 19a may be provided at any position not interfering the operation of the surgeon.

The microscope 1 of the embodiment is characterized in that:

(i) because of non-magnetic material, if the microscope 1 is moved, it does not cause fluctuations of the magnetic field having effect on the image quality of the MRI;

(ii) because of the non-magnet air motor 11, magnetic field is not generated, and adverse effects on the image quality of the MRI from the microscope 11 used most closely to the MRI during operation can be prevented;

(iii) the focus and magnification can be also adjusted manually by turning the knobs 19a, and the operation can be continued even if the air motor 11 fails to run normally thereby a high safety as medical apparatus can be maintained; and (iv) since the exhaust tube 20 is a flexible tube and the exhaust tube 20 is further guided into the arm of the support stand, air noise can be effectively suppressed, and the concentration of the surgeon D during operation is not disturbed.

Figure 6:
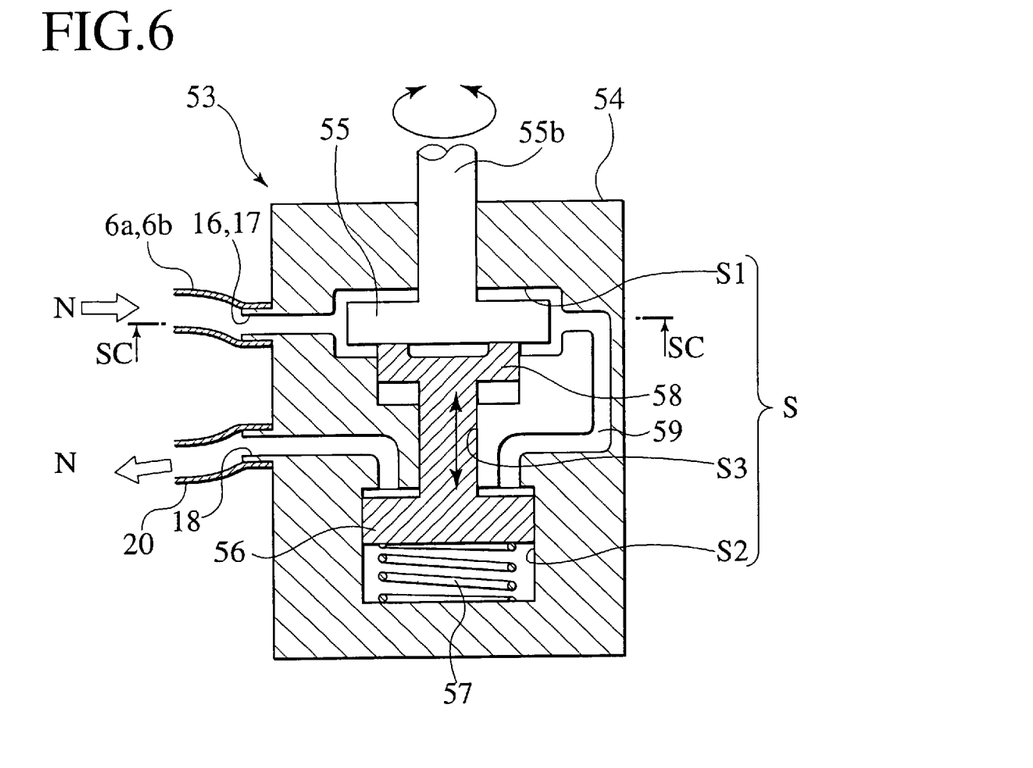
FIG. 6 is a sectional view showing other air motor with brake.
Figure 7:
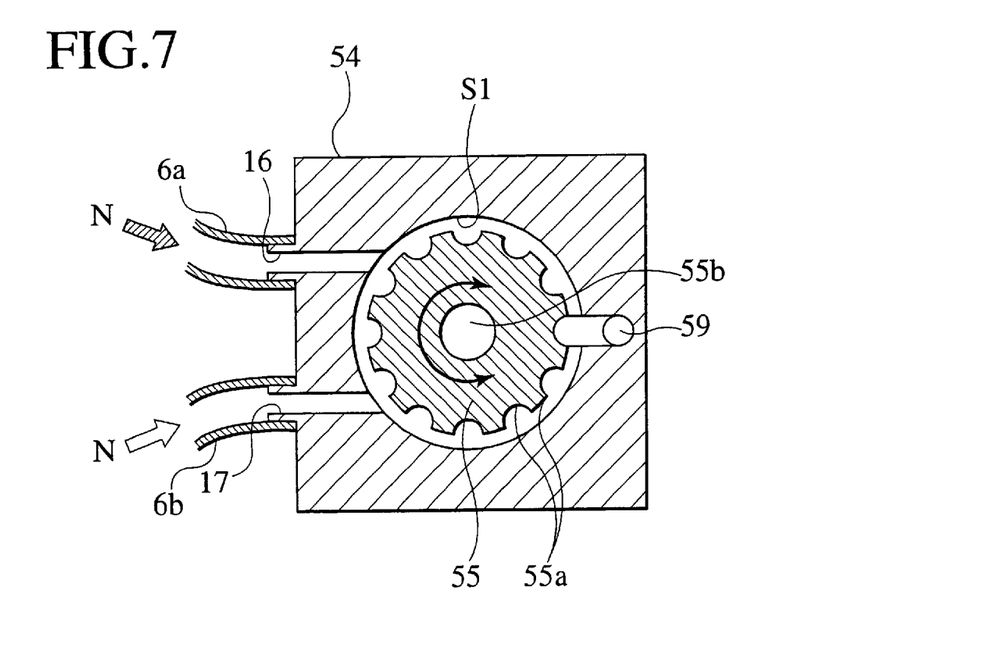
FIG. 7 is a sectional view taken along arrow SC—SC line in FIG. 6.

Next, an air motor 53 with a brake is explained below by referring to FIG. 6 and FIG. 7. Same parts as in the air motor 11 are identified with same reference numerals, and duplicate explanation is omitted.

A turbine 55 accommodated in a space S formed in a housing 54 is flat on the side, and undulations 55a formed on the circumference instead of the blades. In this housing 54, a cylinder chamber S2 is formed aside from the space S1 for accommodating the turbine 55, and a cylinder 56 is accommodated in the cylinder chamber S2 movably parallel substantially to a turbine shaft 55b. In the bottom of the cylinder chamber S2, a spring 57 is provided for thrusting the cylinder 56 to the turbine 55 side.

The space S1 and cylinder chamber S2 are continuous in space through a communicating path S3, in this communication path S3, a brake pad 58 is provided, which moves in a direction along the turbine shaft 55b integrally with the cylinder 56. Usually, therefore, the brake pad 58 is pressed against the side of the turbine 55 by the thrusting force of the spring 57, and prevents rotation of the turbine 55.

An exhaust port 18 is formed from the side surface of the turbine 55 in the cylinder chamber S2 toward the face side of the housing 54. The side surface of the turbine 55 of the cylinder chamber S2 and the space S1 communicate with each other through an exhaust passage 59.

Therefore, when either feed port 16 or 17 is selected, and an air N is supplied from the selected feed port 16 or 17, the air N gets into the turbine 55 side of the cylinder chamber S2 from the space S1 through the exhaust passage 59, and pressure is applied to the cylinder 56 by way of the exhaust passage 59, and the cylinder 56 moves in the direction departing from the turbine 55 by resisting the spring 57. As a result, the brake pad 58 is separated from the turbine 55, and the turbine 55 is in non-braked state, so that the turbine 55 rotates depending on the supply direction of the air N.

When supply of air N is stopped, excess pressure for pushing the cylinder 56 in the departing direction is lost, and the cylinder 56 returns to the initial state by the thrusting force of the spring 57, thereby contacting with the side surface of the turbine 55. Therefore, simultaneously with stopping of air N, the brake pad 58 is brought into contact with the turbine 55, and the rotation of the turbine 55 is stopped immediately, so that excessive rotation by the turbine 55 by its inertia is prevented. Hence, the response of the air motor 53 is improved, and the rotation of the turbine 55 can be controlled accurately only by control of supply and stop of air. Besides, since the response of the air motor 53 is improved, it is not required to decelerate the rotating speed extremely by the gear transmission (see FIG. 2), so that the gear transmission 14 can be reduced in size.

In the embodiment, the microscope for MRI is explained, but the microscope of the invention is not limited to the MRI application only, but may be used in any other application in the environments in which static magnetic field not varying in time is required.

Support Stand

Next, the support stand 2 is explained below by referring to FIG. 8 to FIG. 12. This support stand 2 is preferably used closely to the MRI 3, and is particularly preferred to support the microscope 1. The support stand 2 is supporting the microscope 1 at its leading end, and the surgeon can continue the operation by freely changing the position of the microscope 1. This support stand 2 is generally called the balancing stand, comprising a parallel link constitution and a counter-weight W, and can maintain balance wherever the microscope 1 is located as the "weight." That is, the microscope 1 is supported as if in a weightless state, and the microscope 1 can be moved to a desired position with a relatively small effort.

Figure 8:
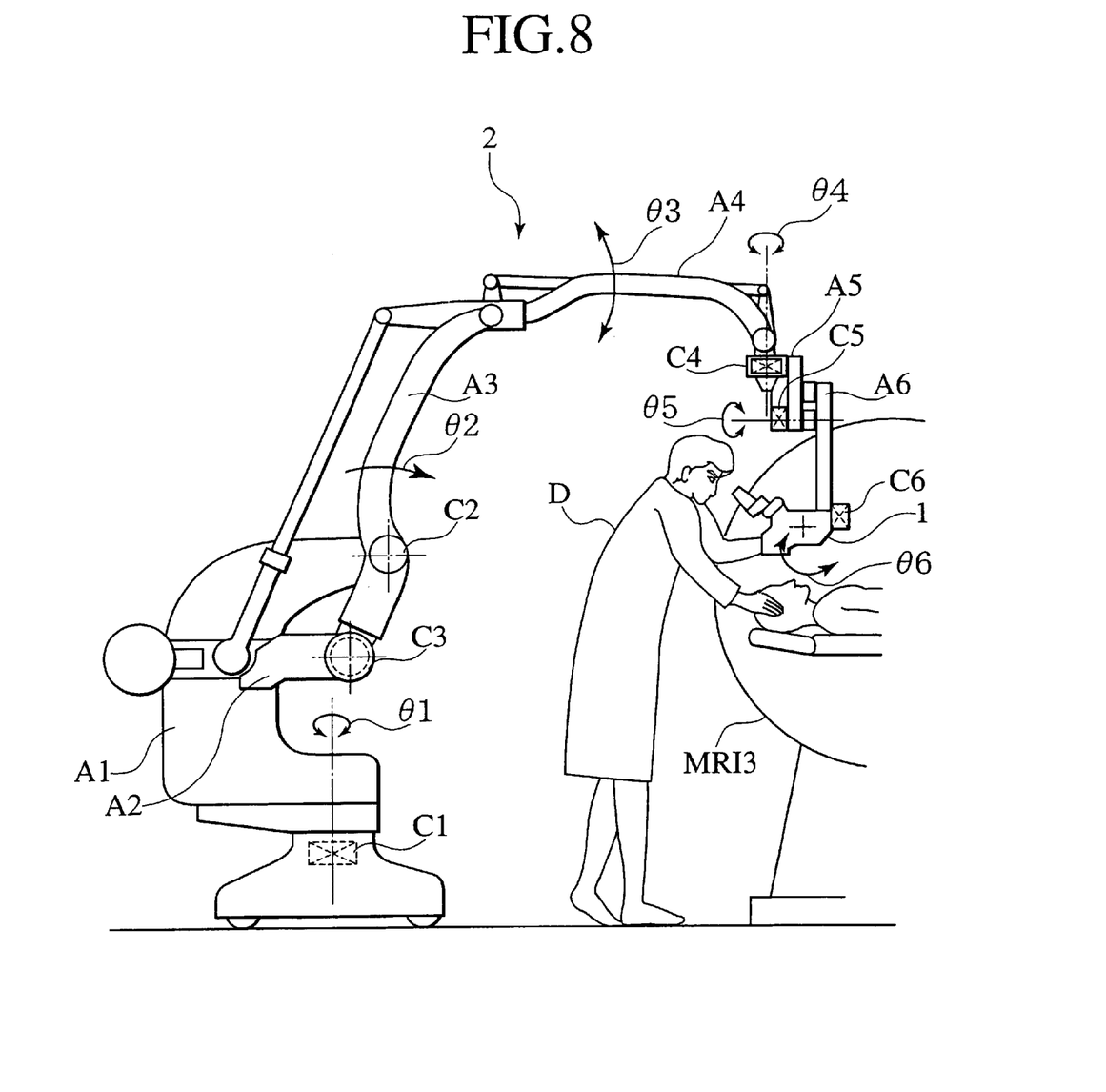
FIG. 8 is a schematic view showing a preferred support stand.

When changing the position of the microscope 1, six air clutches C1 to C6 provided in the support stand 2 are set free, and the position is determined, then the air clutches C1 to C6 are fixed in locked state. In the diagram, the numbers attached to the symbol θ correspond to the members indicated by the numbers C1 to C6 respectively, and the air clutch C1 is for setting the horizontal rotational angle θ1, the air clutch C2 for setting the longitudinal rotational angle θ2, the air clutch C3 for setting the vertical rotational angle θ3, the air clutch C4 for setting the horizontal rotational angle θ4 of the microscope, the air clutch C5 for setting the lateral inclination angle θ5 of the microscope, and the air clutch C6 for setting the tilt angle θ6 of the microscope, either in locked state or in free state.

Figure 9:
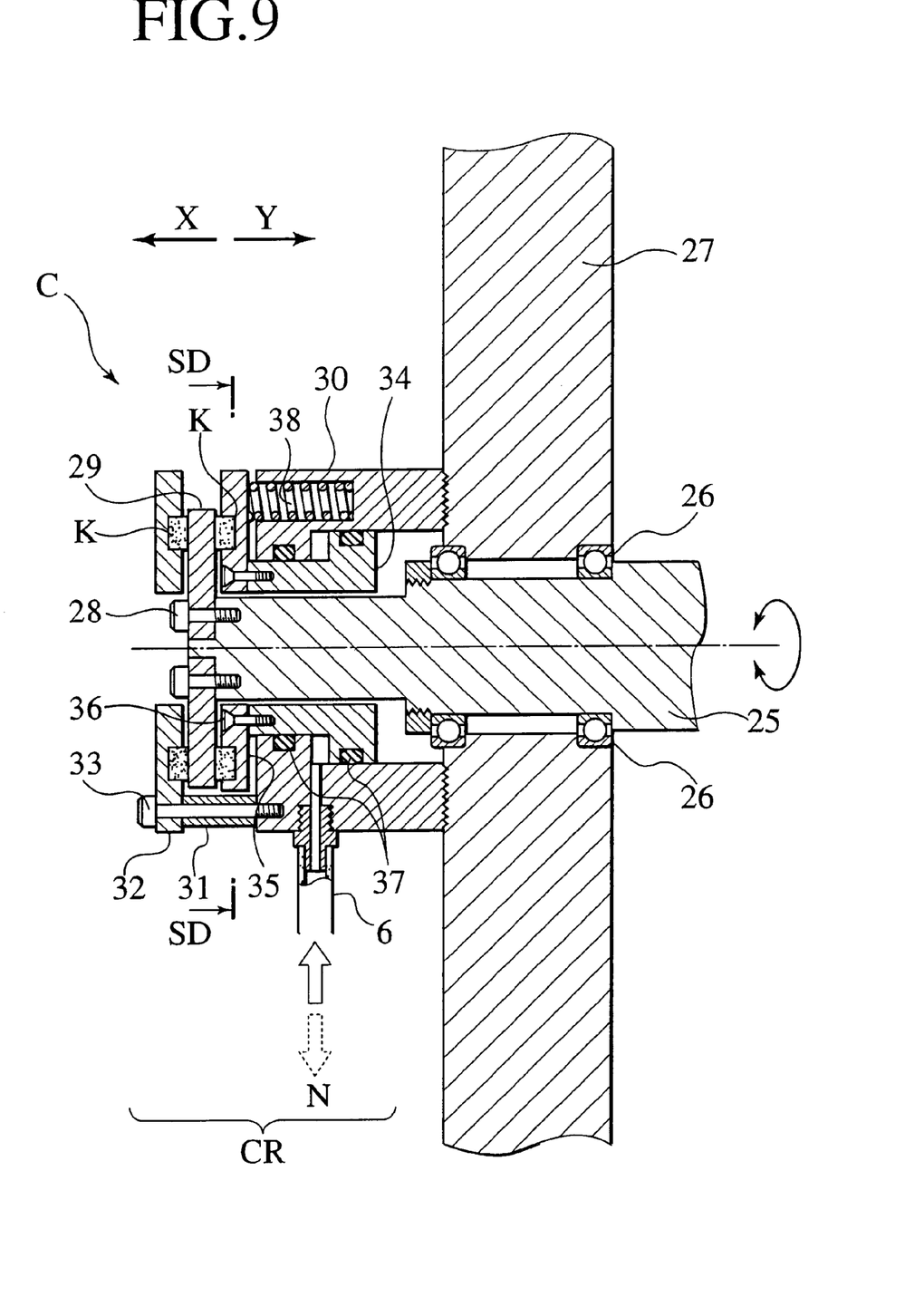
FIG. 9 is a sectional view showing an air clutch preferably used in a support stand.
Figure 10:
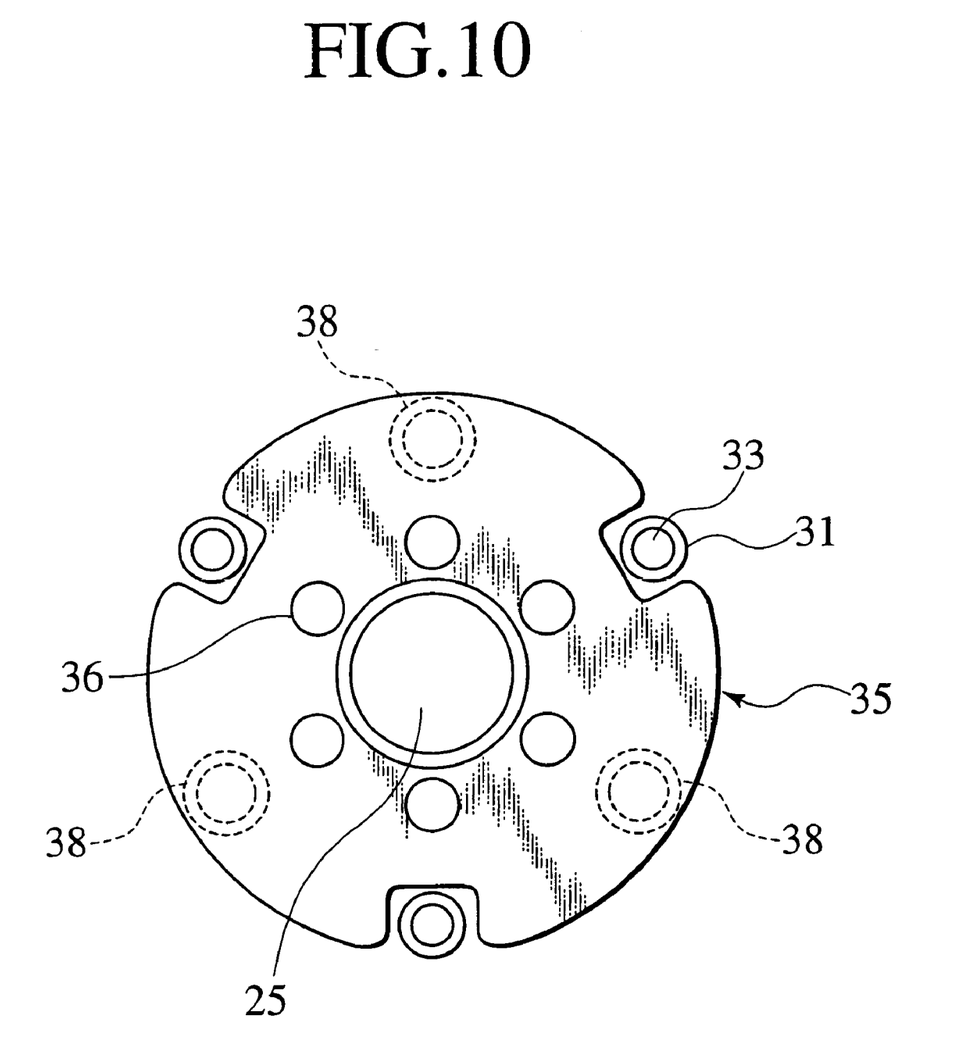
FIG. 10 is a sectional view taken along arrow SD—SD line in FIG. 9.

Hereinafter, the constitution of the air clutch C is explained. A rotary shaft 25 for mounting support arms A1 to A6 of the support stand 2 is supported by a housing 27 of the support arms A1 to A6 by bearings 26. A clutch mechanism CR is provided between the rotary shaft 25 and housing 27. At the leading end of the rotary shaft 25, a disk 29 is fixed by means of bolts 28. On the other hand, a cylinder 30 fixed in the housing 27 is integrally provided with a spacer 31 and a first brake pad 32 by means of bolts 33. Further, in a barrel 34 forming an airtight space in contact with the inner wall of the cylinder 30, a second brake pad 35 is fixed by bolts 36. To enhance the airtight state, an airtight O-ring 37 is provided between the cylinder 30 and barrel 34. The second brake pad 35 is forced in the direction of arrow X in the drawing by means of a spring 38, and the disk 29 is held between the second brake pad 35 and first brake pad 32. As a result, the rotary shaft 25 is usually in locked state. Besides, between the first brake pad 32 and second brake pad 35, and the disk 29, shock absorbing members K are inserted for preventing direct contact.

To operate the air clutch C, the air N is sent into the airtight space. When air N is sent into the cylinder 30 through the tube 6, the barrel 34 is moved in the direction of arrow Y by the applied pressure, and the second brake pad 35 and disk 29 are separated, and the rotary shaft 25 is put in rotatable state. That is, the air clutch C usually maintains the rotary shaft 25 in locked state, and by sending air in operation, it is set in free state. It is locked again by exhausting the air. In case of power failure, the air clutch C maintains the locked state, and the locked state remains when carrying the support stand 2 or mounting the microscope 1, and the mechanism high in safety and reliability is presented.

The tube 6 for supplying and exhausting the air N is provided in the support arms A1 to A6 of the support stand 2, and the air N is exhausted into the support arms A1 to A6.

The support stand 2 of the embodiment is of non-magnet type using air clutch C, and does not generate magnetic field, and therefore if used closely to the MRI, there is no adverse effect on the image quality of the MRI. The support stand 2 is also made of non-magnetic material same as the microscope 1, and if the support stand 2 is moved, it does not cause fluctuation of magnetic field having adverse effects on the image quality of MRI. The support stand 2 is not limited to the balancing stand, but may include any other constitution as far as it is of non-magnet type.

In the embodiment, the support stand used closely to the MRI is explained, but the support stand of the invention is not limited to the MRI application only, but may be used in any other application in the environments in which static magnetic field not varying in time is required.

Figure 11:
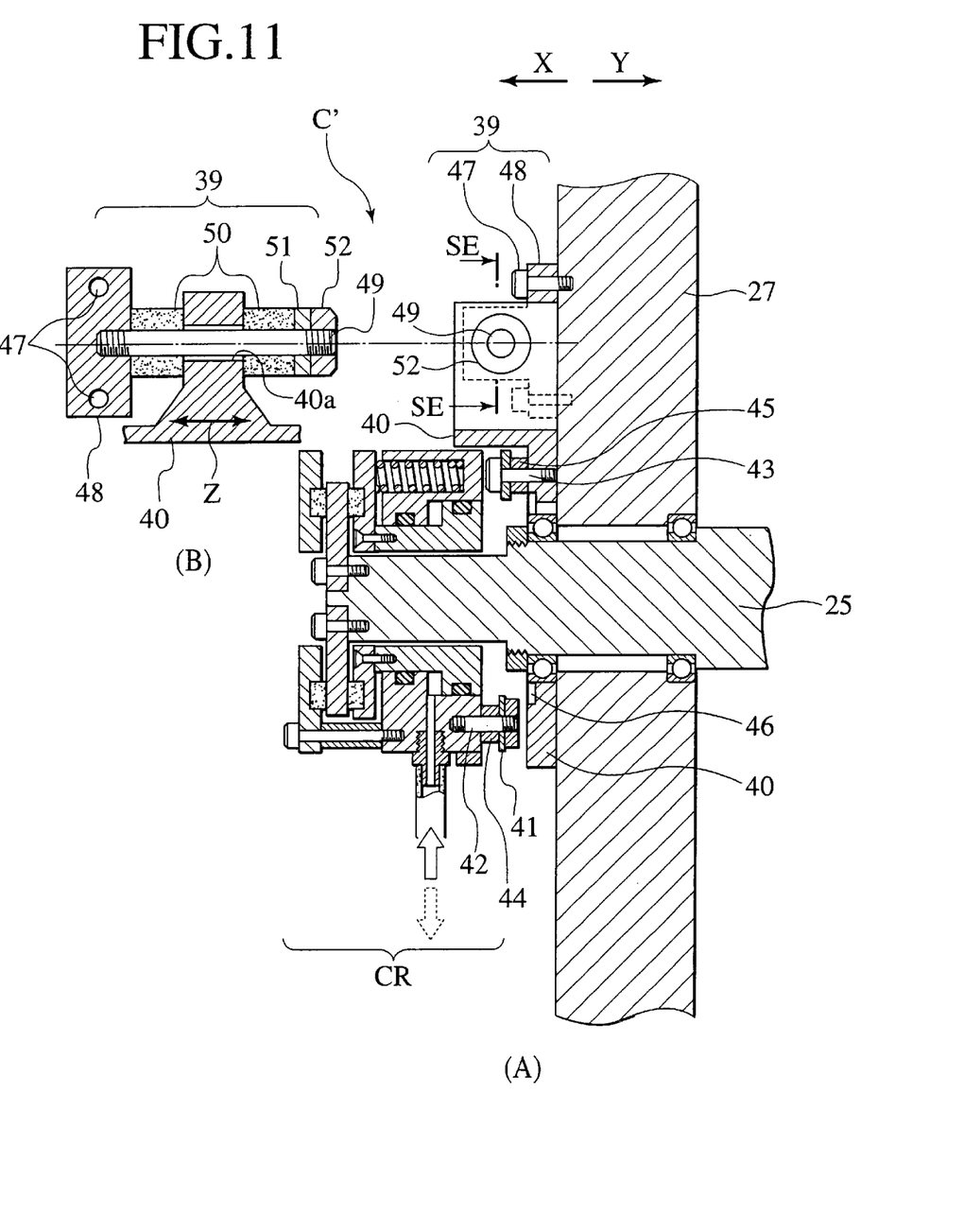
FIG. 11(A) is a sectional view showing other embodiment of air clutch.
FIG. 11(B) is a sectional view taken along arrow SE—SE line in FIG. 11(A)
Figure 12:
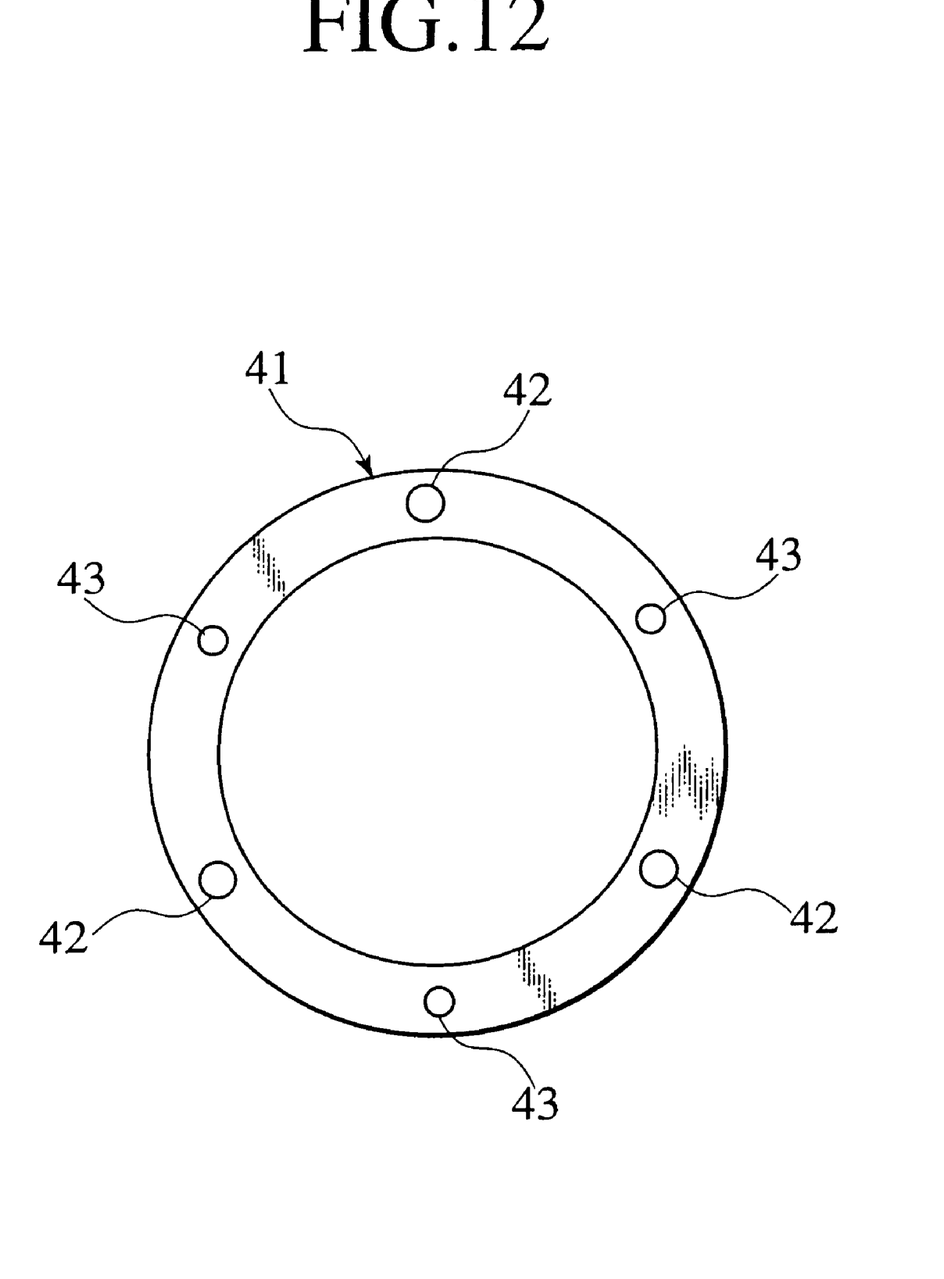
FIG. 12 is a front view of ring plate.

An air clutch C' in other embodiment is explained based on FIG. 11 and FIG. 12. This air clutch C' is same in basic constitution as the air clutch C in FIG. 9 and FIG. 10, but it comprises a shock absorbing mechanism 39 in addition to the clutch mechanism CR. The clutch mechanism CR is same as in FIG. 9, and its constitution and effect are not explained herein. A platform 40 of the shock absorbing mechanism 39 is integrally formed with the clutch mechanism CR by means of ring plate 41, bolts 42, 43, and spacer rings 44, 45, and it is movable in the rotating direction (Z direction) about the rotary shaft 25 in relation to the housing 27. At this time, the platform 40 is not detached from the housing 27 by means of a push ring 46. The platform 40 has a guide hole 40a, as shown in FIG. 11(B), a guide bar 49 of a fixing part 48 fixed to the housing 27 by a bolt 47 is inserted in the guide hole 40a. A cushion member 50 is inserted between the fixing part 48 and platform 40, and other cushion member 50 is also provided at the opposite side, and tightened with a proper pressure by a washer 51 and a nut 52.

In the air clutch C' of the embodiment, when the air N is exhausted in free state, the disk 29 is immediately held between the first brake pad 32 and second brake pad 35, and the shock in the rotating direction (Z direction) at this time is absorbed by the shock absorbing mechanism 39, so that the clutch C' can be operated smoothly.

As described above, nitrogen gas is used as the air, but it is not limited. For example, ordinary air may be used, or any gas maybe used, as far as the turbine 13 or 55 can be rotated.

According to the microscope of the invention, because of non-magnet type not using electric motor, the surrounding magnetic field environments are not varied by focusing or zooming, and when used for MRI, it does not induce fluctuations of magnetic field having effects on the image quality of MRI. Focusing or zooming of the microscope is driven by an air motor, and it can be also driven manually in case of emergency, and therefore the surgical operation can be continued in case of trouble in smooth air supply or air motor operation and the like, so that a high safety is maintained as the medical apparatus. Further, by using a flexible tube at least in part, air is supplied and exhausted in and from the air motor, and air supply noise can be suppressed.

The support stand of the invention comprises plural support arms, at least one rotary shaft for mounting support arms, and a clutch for locking and releasing the rotary shaft, and the clutch is of non-magnet type, and therefore if the clutch is operated, the surrounding magnetic field environments are not changed, and it is suitable for use in close distance to the MRI. In particular, the air clutch is preferred as the clutch, and by disposing the tube for supplying and exhausting air in and from the air clutch in the arm of the support stand, the tube does not interfere when rotating the arm about the rotary shaft of the support stand. Moreover, since the tube is not exposed, the working efficiency of the surgeon is improved, and the arm housing plays the role of silencer and suppresses the noise at low level.

The entire content of a Japanese Patent Applications No. 2000-171277, filed on May 2, 2000 and No. 2001-27154, filed on Feb. 2, 2001 are hereby incorporated by reference.

What is claimed is:

1. A microscope used in a room in which an MRI is installed, comprising:

an air motor applying a torque to a load for manipulation of said microscope through a reduction mechanism; and a manual actuator applying an additional torque to said reduction mechanism, wherein
   the reduction mechanism comprises a transmission having first and second input shafts and an output shaft, the first input shaft receives the torque from the air motor, the second input shaft receives the additional torque from the manual actuator, and the output shaft drives the load for manipulation of the microscope.

2. The microscope according to claim 1, wherein
the load for manipulation of said microscope is a focusing mechanism and a zooming mechanism.

3. The microscope according to claim 1 or 2, wherein
said microscope is formed of non-magnetic material.

4. The microscope according to claims 1 or 2, wherein
a flexible tube is connected to an exhaust port of the air motor and is extended away from an operator of the microscope.

5. The microscope according to claim 4, wherein the flexible tube connected to the exhaust port of the air motor is a silicone tube.

6. The microscope according to claim 1, wherein nitrogen gas is supplied to the air motor for driving the load.

7. The microscope used in a room in which an MRI is installed, comprising:

an air motor driving a load for manipulation of said microscope through a reduction mechanism; and a manual actuator applying an additional torque to said reduction mechanism, wherein said air motor comprises:
   a housing formed with a hollow space;
   a turbine accommodated in said hollow space, said turbine being accommodated rotatably in said hollow space;
   a gas feed port formed in said housing, gas being supplied towards the turbine from said gas feed port and exhausted, said turbine rotating according to a gas feed direction; and
   a brake pad contacting with said turbine with a predetermined urging force, said brake pad departing from said turbine to be in non-contact state by application of exhausted gas pressure.

8. A support stand used in a room in which an MRI is installed comprising:

two or more support arms;
   at least one rotary shaft for pivoting said support arms to each other; and
   an air clutch for locking or releasing said rotary shaft, said air clutch comprising a brake pad and a spring biasing the brake pad to lock the rotary shaft when air is not supplied to the air clutch, wherein the air clutch releases the rotary shaft when air is supplied thereto.

9. The support stand according to claim 8, wherein
a tube for supplying air in and exhausting air from said air clutch is disposed in the support arm.

10. The support stand according to claim 8, wherein
said support stand supports a microscope for controlling a focusing mechanism and a zooming mechanism by means of an air motor.

11. The support stand of claim 8, wherein
said support stand is formed of non-magnetic material.

12. A microscope used in a static magnetic field environment comprising:

a first actuator which does not generate magnetic field, said first actuator applying a torque to a focusing mechanism or a zooming mechanism through a reduction mechanism; and a manual actuator applying an additional torque to said reduction mechanism, said manual actuator being operative at least when said first actuator does not work, wherein
   the reduction mechanism comprises a transmission having first and second input shafts and an output shaft, the first input shaft receives the torque from the first actuator, the second input shaft receives the additional torque from the manual actuator, and the output shaft drives the focusing or zooming mechanism.

* * * * *